(12) United States Patent
Schramm

(10) Patent No.: US 11,701,662 B2
(45) Date of Patent: Jul. 18, 2023

(54) ANALYTE METER AND SYSTEM FOR MEDICAL TESTS

(71) Applicant: Roche Diabetes Care, Inc., Indianapolis, IN (US)

(72) Inventor: Rene Schramm, Heidelberg (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 907 days.

(21) Appl. No.: 16/654,259

(22) Filed: Oct. 16, 2019

(65) Prior Publication Data

US 2020/0122151 A1 Apr. 23, 2020

(30) Foreign Application Priority Data

Oct. 17, 2018 (EP) ...................................... 18201041

(51) Int. Cl.
*B01L 9/00* (2006.01)
*A61B 5/145* (2006.01)
*A61B 5/15* (2006.01)
*A61M 5/172* (2006.01)

(52) U.S. Cl.
CPC ............ *B01L 9/52* (2013.01); *A61B 5/14546* (2013.01); *A61B 5/150358* (2013.01); *A61M 5/1723* (2013.01); *A61M 2230/201* (2013.01); *B01L 2200/025* (2013.01); *B01L 2200/028* (2013.01); *B01L 2200/0689* (2013.01); *B01L 2300/123* (2013.01); *B01L 2300/168* (2013.01)

(58) Field of Classification Search
CPC .......... A61B 5/150358; A61B 5/14546; G01N 27/3273; B01L 9/52; B01L 2300/123; B01L 2200/028; B01L 2300/168; B01L 2200/025; B01L 2200/0689
See application file for complete search history.

(56) References Cited

U.S. PATENT DOCUMENTS

| | | | | |
|---|---|---|---|---|
| 7,842,241 B2 * | 11/2010 | Arbogast | ........... | G01N 33/4875 422/537 |
| 8,145,431 B2 * | 3/2012 | Kloepfer | ................ | G01N 33/66 600/300 |
| 8,158,081 B2 * | 4/2012 | Scott | ................... | G01N 33/4875 422/50 |
| 10,036,709 B2 | 7/2018 | Carter et al. | | |

(Continued)

FOREIGN PATENT DOCUMENTS

| | | |
|---|---|---|
| EP | 2 741 076 | 4/2018 |
| WO | WO 2011/019658 | 2/2011 |

(Continued)

*Primary Examiner* — Shogo Sasaki
(74) *Attorney, Agent, or Firm* — Noodard, Emhardt, Henry, Reeves & Wagner, LLP

(57) ABSTRACT

The invention concerns an analyte meter (10) for medical tests having a meter housing (12), a strip port (14) mounted in an opening of the meter housing (12) and configured to receive a measuring part of a test strip (18), and a sealing insert (16) which is arranged within the strip port (14) and provides an insertion path for the test strip (18). For improved screening against contamination, it is proposed that the sealing insert (16) comprises a plurality of sealing elements (42) which are arranged consecutively along the insertion path, wherein each of the sealing elements (42) has a slit (46) that forms a sealed aperture for the test strip (18) to pass through.

20 Claims, 2 Drawing Sheets

(56) References Cited

U.S. PATENT DOCUMENTS

| | | | |
|---|---|---|---|
| 11,553,861 B1* | 1/2023 | Shah | A61B 5/14532 |
| 2004/0226993 A1* | 11/2004 | Fulcher | G07F 17/24 |
| | | | 235/381 |
| 2009/0270696 A1 | 10/2009 | Arbogast et al. | |
| 2012/0100601 A1 | 4/2012 | Simmons et al. | |
| 2012/0149245 A1 | 6/2012 | Ralston et al. | |
| 2012/0252133 A1 | 10/2012 | Faulkner et al. | |
| 2015/0177174 A1* | 6/2015 | Elder | G01N 33/4875 |
| | | | 205/792 |
| 2017/0219555 A1 | 8/2017 | Nazzaro et al. | |
| 2017/0343504 A1* | 11/2017 | Davies | G01N 27/3273 |
| 2018/0135098 A1* | 5/2018 | Messinger | A61B 5/0002 |

FOREIGN PATENT DOCUMENTS

| | | |
|---|---|---|
| WO | WO 2015/023611 | 2/2015 |
| WO | WO 2017/205754 | 11/2017 |

* cited by examiner ial relates to an analyte meter for medical tests
ANALYTE METER AND SYSTEM FOR MEDICAL TESTS The invention relates to an analyte meter for medical tests having a meter housing, a strip port mounted in an opening of the meter housing and configured to receive a measuring part of a test strip, and a sealing insert which is arranged within the strip port and provides an insertion path for the test strip. The invention further concerns a system including such an analyte meter.

US 2012/0100601 A1 discloses a modular analyte measurement system having a strip port interface that guides fluid away from the strip port opening, as well as absorptive elements that prevent fluid from entering the strip port. However, providing alternative fluid paths to guide fluid external to the device requires complicated construction measures.

On this basis an object of the invention is to further improve the known analyte meters and systems to limit the potential for contamination of internal components and to avoid interference of measuring results with limited manufacturing expenditure.

The combination of features stated in the independent claims is proposed to achieve this object. Advantageous embodiments and further developments of the invention are derived from the dependent claims.

The invention is based on the idea of providing successive sealing barriers in the insertion path of the test strip. Thus, a glucose test arrangement is proposed in which the sealing insert comprises a plurality of sealing elements which are arranged consecutively as seen along the insertion path, wherein each of the sealing elements has a slit that forms a sealed aperture for the test strip to pass through. In this way, it is possible to efficiently prevent liquids, moisture, humidity, dust, dirt and/or other environmental materials from entering the inside of the meter housing through the test strip port. In particular, as required by regulatory provision for medical devices, effective protection can be provided against ingress of dripping water. Furthermore, the successive slits effectuate the multiple wipe-off of potential contaminant substances from the test strip surface materials, while intercepting or collecting spaces can be provided between the sealing elements. At the same time, it is possible to use non-variable parts for the multiple sealing elements, thus simplifying the production and assembly.

Advantageously, the sealing elements are spaced apart from each other by means of a spacer configuration. This allows to create defined spaces to collect contaminants with simple construction measures.

A further improvement provides that a gap for collecting contaminant substances from the test strip is maintained between neighboring sealing elements, the gap having a width of less than 1.0 mm, preferably between 0.2 and 0.5 mm. By these measures, capillary forces can support the collection of unwanted liquids.

As a still further advantageous measure, the sealing elements each are provided with a plurality of parallel distance rips protruding from a flat base part which defines the slit, the distance rips extending transversely to the longitudinal direction of the slit. Thereby, separate channels are provided for transporting fluid away from the test strip.

Advantageously, the sealing elements are made of an elastomeric material as separately formed, preferably injection moulded parts.

In order to further simplify assembly and replacement, it is advantageous if the sealing elements are detachably connected to each other by means of a coupling connection.

To provide an undisturbed insertion path for the test strip, it is proposed that the sealing elements are provided in a stacked configuration on positioning pins such that the slits are aligned to each other.

For improved use convenience, it is advantageous if the sealing elements are at least partially made of a transparent material so as to allow for illumination of the strip port and/or the test strip by a light source being arranged inside the meter housing.

Another improvement in this direction provides that the sealing elements are formed integral with a light guide, the light guide being coupled to a light source inside the meter housing.

In order to avoid damage of the sealing elements by sharp strip edges, it is it is advantageous if the width of the slit between its longitudinal ends is more than 5%, preferably more than 10% larger than the width of the test strip.

For improved screening, it is it is advantageous if the sealing elements each have a pair of bendable sealing lips which confine the slit on its long sides.

Advantageously, the strip port has a key portion which can be combined in a positive fit with a structure of the housing, thus preventing erroneous assembly of unsuitable components.

For further improvement of the shielding capabilities, one of the sealing elements can be fixedly attached preferably by an adhesive to a receiving frame of the strip port.

A still further improvement in connection with a remote medication delivery device, such as an insulin delivery device provides that a remote control is included in the analyte meter.

Another aspect of the invention concerns an analyte measurement system for medical tests comprising the analyte meter of any of the previous claims as a handheld unit and a disposable test strip which is received in the strip port of the analyte meter and can be loaded with a sample of a body fluid.

In the following, the invention is further elucidated on the basis of an embodiment example shown schematically in the drawings, where FIG. 1 is a perspective view of an analyte (glucose) meter;

Figure 1:
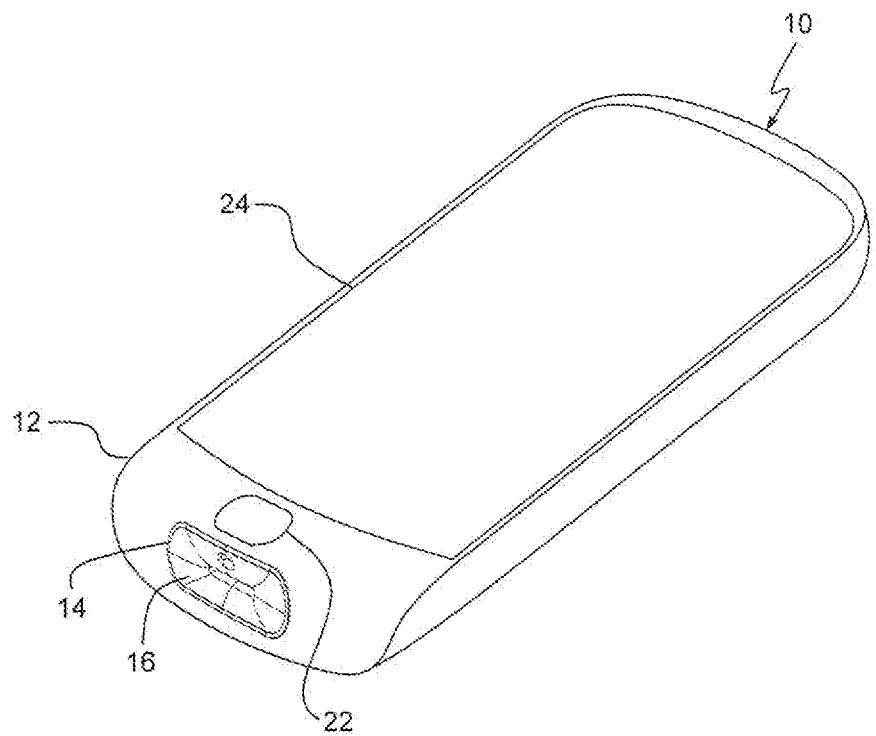
Figure 2:
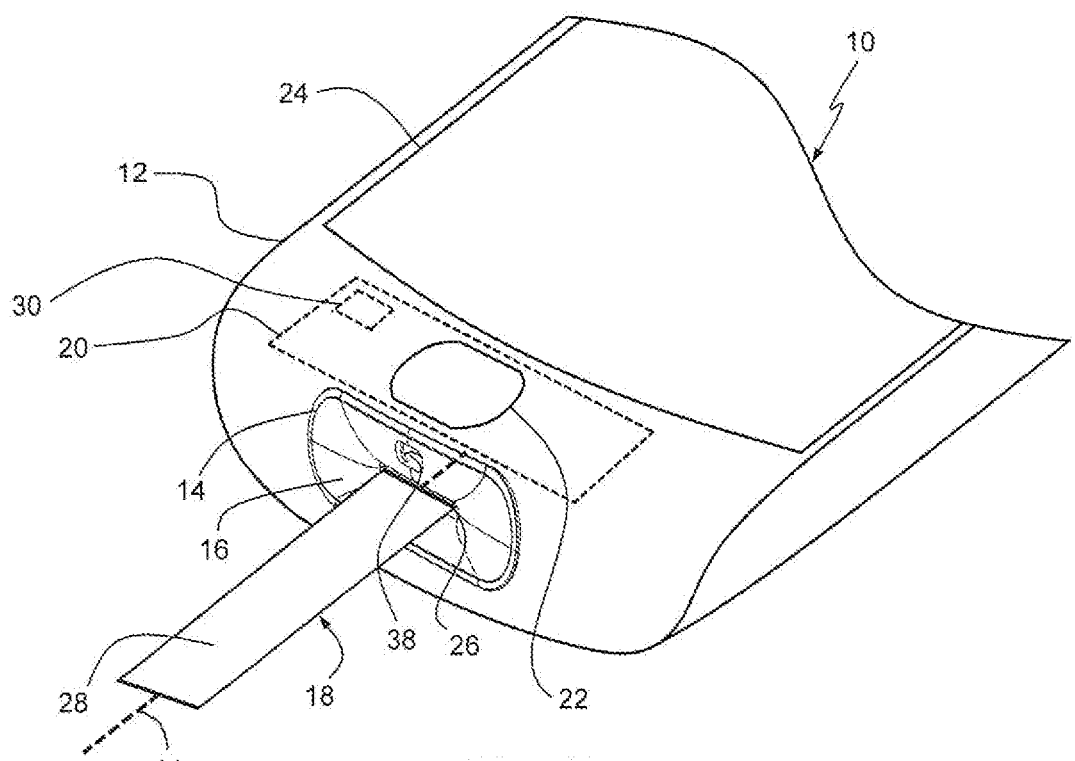
FIG. 2 is a partial enlarged, cut-out view of the meter of FIG. 1 with a test strip in a strip port.

As depicted in FIGS. 1 and 2, an exemplary embodiment of a portable analyte meter 10 for blood glucose tests comprises a meter housing 12 and a strip port 14 which is mounted in an opening of the meter housing 12 and includes a sealing insert 16 for providing a sealed insertion path for a disposable test strip 18.

The meter 10 further comprises measuring electronics on an inner circuit board 20, operating controls 22 and a display 24 for displaying measuring results. to.

As shown, the meter 10 and the test strip 18 complement to a system which allows a user to take analyte measurements on body fluids and specifically glucose measurements on a blood sample on-the-spot. For this purpose, a measuring part 26 of the test strip 18 is inserted through the sealing insert 16 into the meter housing 12, while a blood sample is applied to an inner capillary channel opening at the handling part 28 of the test strip 18 which sticks out of the meter housing 12. The measurement is based on an electrochemical strip design, which is well known known per se.

The analyte meter 10 may also include or act as a remote control 30 for a separate medication delivery device, such as an insulin delivery pump (not shown), thus both the meter and the pump fulfilling regulatory requirements for medical devices.

Figure 3:
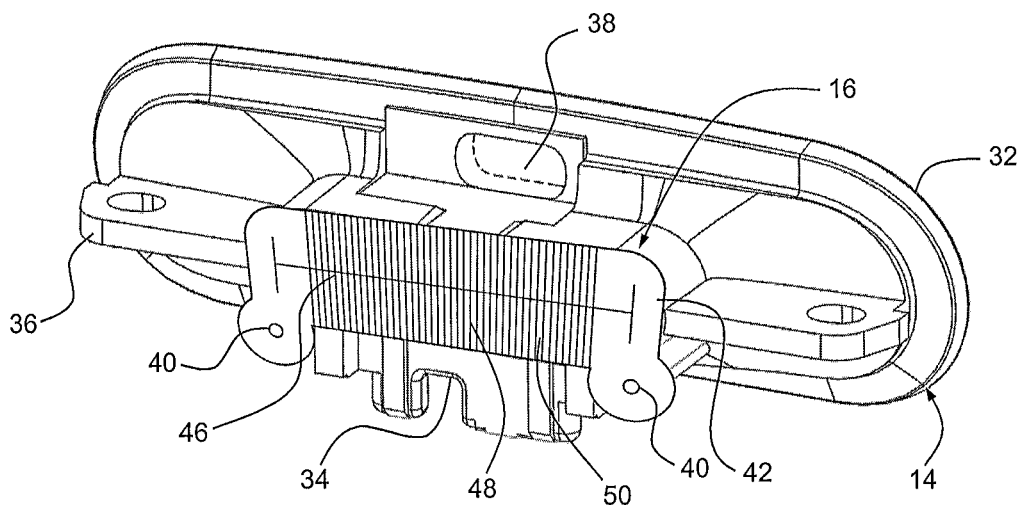
FIG. 3 is a rear perspective view of a strip port of the meter of FIG. 1.

FIG. 3 shows the strip port 14 and the sealing insert 16 from the rear side which joins into the meter housing 12 in more detail. A rigid frame 32 is provided with a key portion 34 which can be combined in a positive fit with a receiving structure of the housing 12 thereby avoiding that an inappropriate unit is inadvertently mounted during manufacture or repair of the meter. The frame 32 has protruding nosepieces 36 which allow a snap-on connection to the meter housing 12 and maintain a distance to the circuit board 20. A light-guide 38 above the sealing insert 16 can be coupled to an LED light source on the circuit board 20 in order to illuminate the handling part 28 of the test strip 18.

The sealing insert 16 is mounted on positioning pins 40 which stick out from the frame 32 into the housing interior. While two pins 40 are shown, it is also conceivable to provide more pins, e.g. four distributed pins for an even more secure positioning. On the pins 40, there is mounted a plurality of sealing elements 42 in a stacked configuration, thereby forming the sealing insert 16. The sealing elements 42 are arranged consecutively as seen along the insertion path 44 of the test strip 18, as shown in depicted in FIG. 2. Each of the sealing elements 42 has a slit 46 that forms a sealed aperture for the test strip 18 to pass through. The positioning by means of the pins 40 ensures that the slits 46 are aligned to each other falling in line in a common plane.

As explained in more detail below, the sealing elements 42 each are provided with a plurality of parallel distance rips 48 protruding from a flat base part 50 which defines the slit 46, where the distance rips 48 extend transversely to the longitudinal slit direction.

Figure 4:
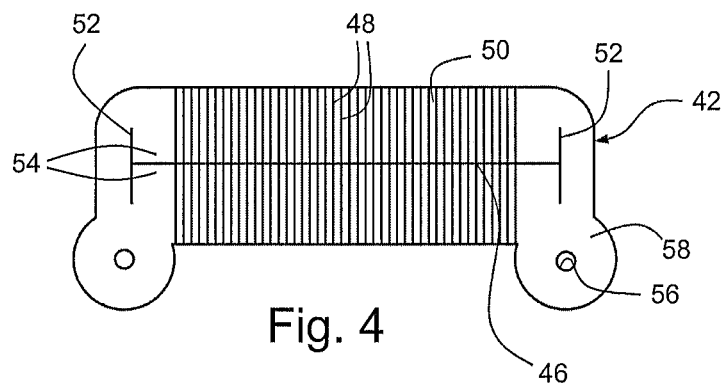
FIG. 4 is a plan view of a sealing element of the strip port of FIG. 3.

As depicted in FIG. 4, the sealing elements 42 can be made as same parts, e.g. from an elastomeric material by injection moulding. Then, the slit 46 is cut into the moulded part and terminated by two smaller, perpendicular cuts 52. In this way, a pair of bendable sealing lips 54 is created which confine the slit 64 on its long sides. In the mounted state, the sealing elements 42 are detachably connected to each other by the coupling connection provided by the pins 40 which reach through eyes 56 in protrusions 58 of the base part 50. Thereby, it is readily conceivable to replace or additionally mount the sealing elements 42. For a further tightening on the side of the meter housing 12, it is also possible to circumferentially adhere the outer sealing element 42 to the frame 32.

In an advantageous embodiment, the sealing elements 42 are formed integral with the light guide 38 e.g. by two-component injection moulding. It is also possible that the sealing elements 42 are at least partially made of a transparent material so as to allow for illumination of the strip port 14 and/or the test strip 18.

Figure 5:
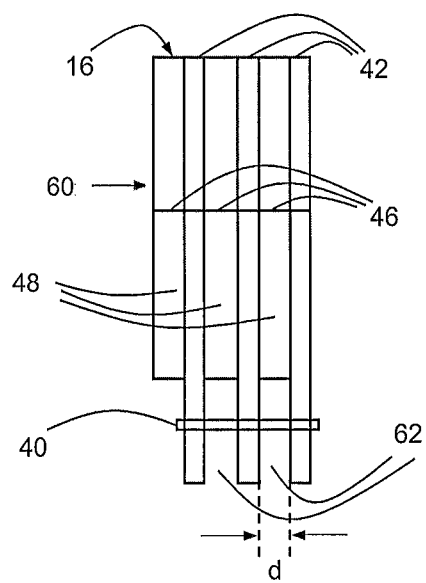
FIG. 5 is a side view of a consecutive arrangement of three sealing elements in a sealing insert of the strip port of FIG. 3.

As illustrated in FIG. 5, the three sealing elements 42 of the sealing insert 16 are spaced apart from each other by means of the spacer-grid 60 provided by the rips 48. Thus, a gap 62 for collecting contaminant substances wiped-off from the test strip 18 is maintained between neighboring sealing elements 42. In order to support capillary action, the gap should have a width d between 0.2 and 0.5 mm.

The invention claimed is:

1. An analyte meter for medical tests comprising:
a meter housing,
a strip port mounted in an opening of the meter housing and configured to receive a measuring part of a test strip, and
a sealing insert which is arranged within the strip port and provides an insertion path for the test strip, the sealing insert comprising a plurality of sealing elements which are arranged consecutively along the insertion path, wherein each of the sealing elements has a slit that forms a sealed aperture for the test strip to pass through.

2. The analyte meter of claim 1, wherein the sealing elements are spaced apart from each other by means of a spacer configuration.

3. The analyte meter of claim 1, wherein a gap for collecting contaminant substances from the test strip is maintained between neighboring sealing elements, the gap having a width of less than 1.0 mm.

4. The analyte meter of claim 1, wherein the sealing elements each are provided with a plurality of parallel distance rips protruding from a flat base part which defines the slit, the distance rips extending transversely to the longitudinal direction of the slit.

5. The analyte meter of claim 1, wherein the sealing elements are made of an elastomeric material as separately formed, preferably injection moulded parts.

6. The analyte meter of claim 1, wherein the sealing elements are detachably connected to each other by means of a coupling connection.

7. The analyte meter of claim 1, wherein the sealing elements are provided in a stacked configuration on positioning pins such that the slits are aligned to each other.

8. The analyte meter of claim 1, wherein the sealing elements are at least partially made of a transparent material so as to allow for illumination of the strip port and/or the test strip by a light source being arranged inside the meter housing.

9. The analyte meter of claim 1, wherein the sealing elements are formed integral with a light guide which is coupled to a light source inside the meter housing.

10. The analyte meter of claim 1, wherein the width of the slit between its longitudinal ends is more than 5% larger than the width of the test strip.

11. The analyte meter of claim 1, wherein the sealing elements each have a pair of bendable sealing lips which confine the slit on its long sides.

12. The analyte meter of claim 1, wherein the strip port has a key portion which can be combined in a positive fit with a lock structure of the housing.

13. The analyte meter of claim 1, wherein at least one of the sealing elements is fixedly attached preferably by an adhesive to a receiving frame of the strip port.

14. The analyte meter of claim 1, further comprising a remote control for a remote medication delivery device, such as an insulin delivery device.

15. The analyte meter of claim 3 wherein the gap having a width of between 0.2 and 0.5 mm.

16. The analyte meter of claim 10 wherein the width of the slit between its longitudinal ends is more than 10% larger than the width of the test strip.

17. An analyte meter for medical tests comprising:
a meter housing,
a strip port mounted in an opening of the meter housing and configured to receive a measuring part of a test strip, and
a sealing insert which is arranged within the strip port and provides an insertion path for the test strip, the sealing insert comprising a plurality of sealing elements which are arranged consecutively along the insertion path, wherein each of the sealing elements has a slit that forms a sealed aperture for the test strip to pass through, wherein the sealing elements are provided in a stacked configuration such that the slits are aligned to each other, and wherein the sealing elements are spaced apart from each other by means of a spacer configuration, the spacer configuration providing gaps between the sealing elements.

18. The analyte meter of claim 17 wherein the gaps having a width of less than 1.0 mm.

19. The analyte meter of claim 17 wherein the width of the slits between their longitudinal ends is more than 5%, larger than the width of the test strip.

20. An analyte measurement system for medical tests comprising the analyte meter of claim 1 as a handheld unit and a disposable test strip which is received in the strip port of the analyte meter and can be loaded with a sample of a body fluid.

\* \* \* \* \*